(12) United States Patent
Ho et al.

(10) Patent No.: US 8,753,541 B2
(45) Date of Patent: Jun. 17, 2014

(54) DEVELOPMENT OF PHOPHOLIPID-CAPPED GOLD NANOPARTICLES (PLGNPS) AS SURFACE ENHANCED RAMAN SCATTERING PROBES

(75) Inventors: Ja-An Ho, Hsinchu (TW); Si-Han Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 734 days.

(21) Appl. No.: 12/857,327

(22) Filed: Aug. 16, 2010

(65) Prior Publication Data
US 2011/0089379 A1    Apr. 21, 2011

(30) Foreign Application Priority Data

Oct. 19, 2009    (TW) .............................. 98135255 A

(51) Int. Cl.
*G01N 21/01*    (2006.01)
*B82Y 15/00*    (2011.01)
*B82Y 40/00*    (2011.01)

(52) U.S. Cl.
USPC ........ 252/408.1; 977/773; 977/783; 977/797; 977/810; 977/895; 977/953; 977/958

(58) Field of Classification Search
USPC ............... 252/408.1; 977/773, 783, 797, 810, 977/895, 953, 958
See application file for complete search history.

(56) References Cited

U.S. PATENT DOCUMENTS 7,333,197 B2    2/2008   Fritz et al. ..................... 356/338

OTHER PUBLICATIONS

H. Y. Chen et al., Encapsulation of Single Small Gold Nanoparticles by Diblock Copolymers, 9 CHEMPHYSCHEM 388-392 (2008).*

* cited by examiner

*Primary Examiner* — Randy Boyer
(74) *Attorney, Agent, or Firm* — WPAT, P.C.; Anthony King; Kay Yang

(57) ABSTRACT

The molecule is prepared by capping phospholipid on a single gold nanoparticle (GNP). Since the thiol-related molecule bounded on GNP shows the characteristic of surface-enhanced Raman scattering (SERS), the phospholipid-capped gold nanoparticle (PLGNP) can be formed as a nanoprobe applied on the detection device integrating optics and chemistry and used in the fields of biomedicine, medical diagnosis and environment for detecting, such as solutions containing salts or proteins.

20 Claims, 5 Drawing Sheets

DEVELOPMENT OF PHOPHOLIPID-CAPPED GOLD NANOPARTICLES (PLGNPS) AS SURFACE ENHANCED RAMAN SCATTERING PROBES

FIELD OF THE INVENTION

The present invention relates to a signaling molecule, particularly to an enhanced Raman scattering signaling molecule, which is single gold nanoparticle bound to a thiol molecule being encapsulated with phospholipid capping. Since the thiol molecule represents the characteristic of Raman signal, the signaling molecule acts as the material having the surface enhanced Raman scattering and can be applied in the detection apparatus combining optics and chemistry.

BACKGROUND OF THE INVENTION

Gold nanoparticles (GNPs) attract much interest because of their electronic, optical, thermal and catalytic properties as well as their biocompatibility and low toxicity, which have greatly impacted the biological fields of imaging, sensing and medicine in recent years (Jain et al., 2008) to detect chemicals in the sample, or microbes or particular molecules in the cells. However, GNPs only can achieve the specific sensitivity and detection limits. Energy is released by scattering if the molecules cannot absorb the photons' energy after the incident photons bombards to the molecules. Since most scattering belongs to Rayleigh scattering and Raman scattering accounts for $1/1000$ of Rayleigh scattering, Raman scattering becomes the excellent tools for detecting molecular sensitivity and detection limits.

Surface enhanced Raman scattering (SERS) is a surface sensitive technique that results in effective enhancement of the Raman scattering for molecules in the vicinity of the surface of particles for $10^5 \sim 10^6$ times (Schatz, 1984). The most common application of combining SERS and GNP is to prepare the SERS nanoprobes which is to attach the Raman reporter onto the surface of metal nanoparticles, such as the thiol-related ligands bound to the surface of particles (Chompoosor et al., 2008; Hong et al., 2006). Several methods have been developed to stabilize the nanoprobes (i.e. nanoparticle-thiol molecule) by coating a shell, such as Silica (Mulvaney et al., 2003) and copolymers (Yang et al., 2009) onto the nanoprobes.

U.S. Pat. No. 7,333,197 discloses a flow cytometry based on Raman detection, wherein cells or particles are coated with a colloidal aggregate, the colloid-coated cells or particles are dispersed, and then the emitted surface enhanced Raman scattering is detected using the flow cytometry. However, cells or particles do not bound to the molecules carrying thiol signals, and cells or particles cannot completely separate individually, so as to result in the disturbance of signal detection.

Since the multiple nanoparticles are capped and usually aggregates in the prior art, the quantitative object to control the particular amount of nanoparticles cannot be achieved. Therefore, the technique which the single GNP is capped and can still represent Raman signal would be applied on the detection apparatus, would be applied on related detection for sera and cellular media containing salts or proteins, and have great benefit in the fields of biomedicine, medical diagnosis and environment.

It is therefore attempted by the applicant to deal with the above situation encountered in the prior art.

SUMMARY OF THE INVENTION

An enhanced Raman scattering signaling molecule is provided in the present invention, where the signal gold nanoparticle bound to the thiol molecules is encapsulated with phospholipid capping. The signaling molecule becomes a material having surface enhanced Raman scattering and can be applied on the detection device integrating optics and chemistry since the thiol molecule owns the characteristic of Raman signal. Since GNP is encapsulated with phospholipid capping, the enhanced Raman scattering signaling molecule is relatively stable in the bio-system to be applied on the related detection for sera and cellular media. Comparing with other products which cannot maintain their stability in the sample containing salts or proteins, the signaling molecule of the present invention would be widely applied in the fields of biomedicine, medical diagnosis and environment.

A method for preparing a signaling molecule including a metal nanoparticle is provided in the present invention. The method includes steps of: (a) treating a surface of the metal nanoparticle with an acidic solution; (b) resolving the metal nanoparticle in a dimethylformamide (DMF) to obtain a first intermediate; (c) adding a phospholipid and a thiol molecule to the first intermediate to perform a heating process to obtain a second intermediate; and (d) separating the second intermediate to obtain the signaling molecule including the metal nanoparticle.

Preferably, the step (a) further includes steps of: (a1) centrifuging the metal nanoparticle; and (a2) removing the acidic solution. The step (a2) is performed by a decantation.

Preferably, the step (c) further includes a step of (c1) adding a water having a temperature the same in the step (c) to result in a water-DMF volume ratio of 1:1. The preheating step is performed before the step (c). The heating process in the step (c) is ranged between 60° C. and 100° C., and the temperature of the heating process is preferably at 80° C.

Preferably, the step (d) is performed to remove a non-signaling molecule in the second intermediate by a centrifugation or a decantation.

Preferably, the acidic solution is a citric acid solution.

Preferably, the metal nanoparticle is one selected from a group comprises a gold, a silver, a aluminum and a platinum.

Preferably, the metal nanoparticle is a gold nanoparticle.

Preferably, the phospholipid includes a dipalmitoylphospho-phatidylcholine (DPPC), and a dipalmitoylphosphatidylgly-cerol (DPPG). The DPPC-DPPG molar ratio is 10:1~14:1, and DPPC and DPPG are resolved in the DMF.

Preferably, the thiol molecule is a 2-naphthalenethiol.

Preferably, the signaling molecule has the surface enhanced Raman scattering ability.

Preferably, the signaling molecule encapsulates a gold nanoparticle.

A signaling molecule is further provided in the present invention and includes: a metal nanoparticle; a thiol molecule bound to the surface of the metal nanoparticle; and a phospholipid capping the metal nanoparticle and the thiol molecule, wherein a number of the metal nanoparticle is single, and the signaling molecule has a surface enhanced Raman scattering ability.

Preferably, the metal nanoparticle is one selected from a group comprises a gold, a silver, a aluminum and a platinum.

Preferably, the metal nanoparticle is a gold nanoparticle, and the thiol molecule is a 2-naphthalenethiol.

Preferably, the phospholipid comprises a dipalmitoylphosphophatidylcholine (DPPC), a dipalmitoylphos-phatidylglycerol (DPPG) or a 1,2-dihexadecanoyl-sn-glycero-3-phosphoethanol-amine-N-[4-(p-maleimidomethy) cyclohexanecarboxamide] (PE-MCC) or other phospholipids such as, 1,2-di-oleoyl-sn-glycero-3-phosphocholine (DOPC).

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

I. Preparation of Phospholipid-Capped Gold Nanoparticle (PLGNP)

Figure 1:
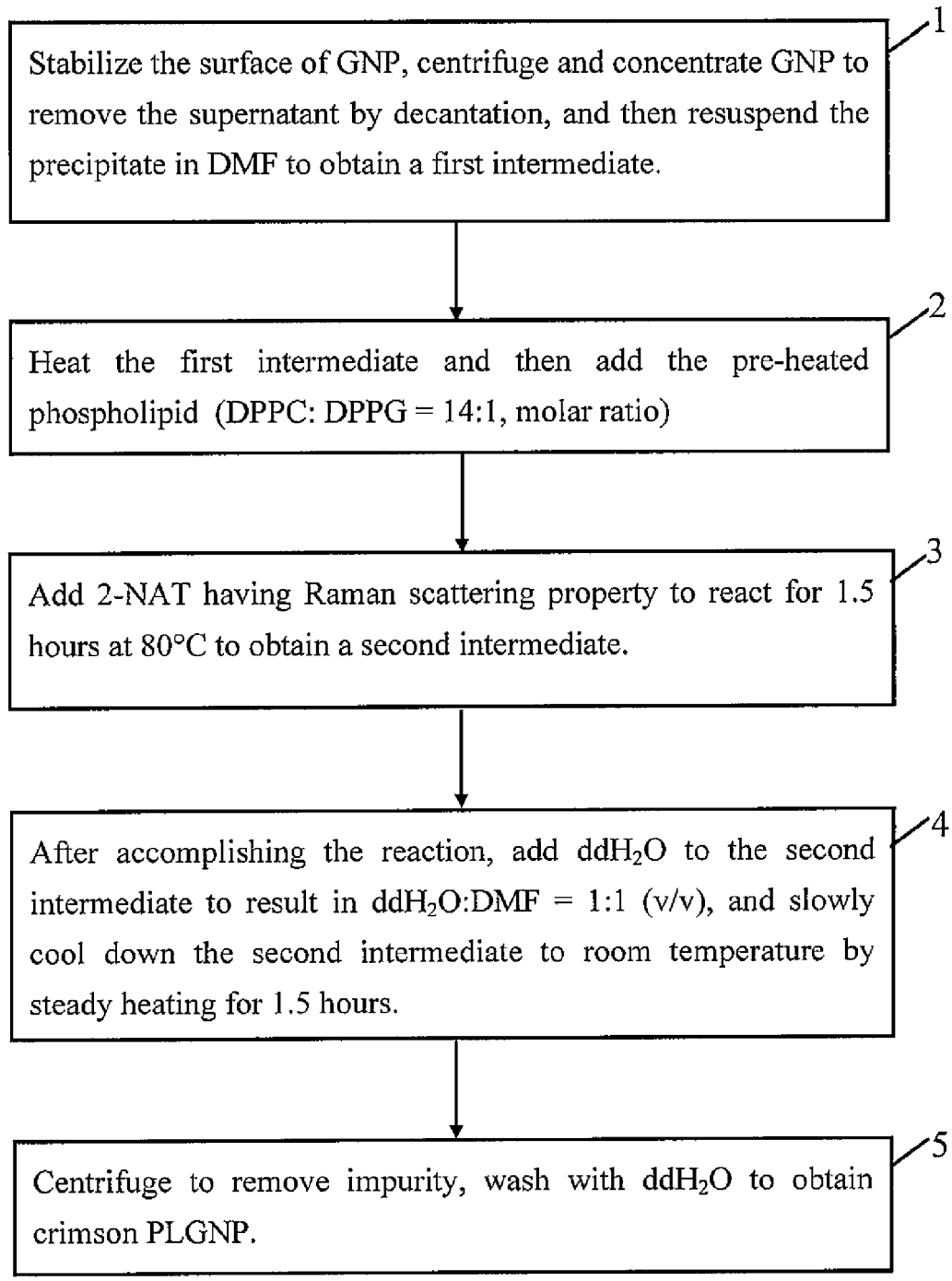
FIG. 1 represents the preparation process for SERS signaling molecule.

Please refer to FIG. 1, which is the preparation process for the surface enhanced Raman scattering (SERS) signaling molecule. First, the surface of gold nanoparticle (GNP) is stabilized with citric acid. GNP is concentrated using centrifugation, and the supernatant then is removed by decantation. The precipitate is resolved using dimethylformamide (DMF) to obtain a first intermediate (step 1). Then the first intermediate containing GNPs are heated in the water bath of 60° C.~100° C., in which the temperature is preferably set at 80° C. Next, phospholipid is added, wherein phospholipid is preferably preheated in the water bath of 60° C.~100° C. before phospholipid is added to the first intermediate. Phospholipid mainly includes dipalmitoylphosphophatidylcholine (DPPC), dipalmitoylphosphatidylgly-cerol (DPPG), both of which is resolved in DMF and the DPPC-DPPG molar ratio in DMF is 14:1 (step 2). The thiol molecules (5 µl) with characteristic of Raman intensity, i.e. 2-naphthalenethiol (2-NAT) resolved in DMF and at 62.5 mM, are added after the solution is uniformly mixed. The solution is reacted for 1.5 hours at 60° C.~100° C. to obtain a second intermediate (step 3). After the above-mentioned first staged reaction is accomplished, 800 µl deionized water (ddH$_2$O) of 60° C.~100° C. is added to the second intermediate and a ddH$_2$O-DMF volume ratio is adjusted to 1:1. The second intermediate is gradually cooled down to room temperature in the water bath post 1.5-hour heating at 60° C.~100° C. (step 4). To separate PLGNPs with the hollow liposome, the unreacted thiol molecules and DMF, the second intermediate is centrifuged at 16,000 rpm for 10 minutes and resuspended in 1 ml ddH$_2$O for thrice after the supernatant is removed (using decantation). Finally, the purified crimson nanoparticles are PLGNPs (4.4×10$^{12}$ particles mL$^{-1}$) (step 5).

Figure 2:
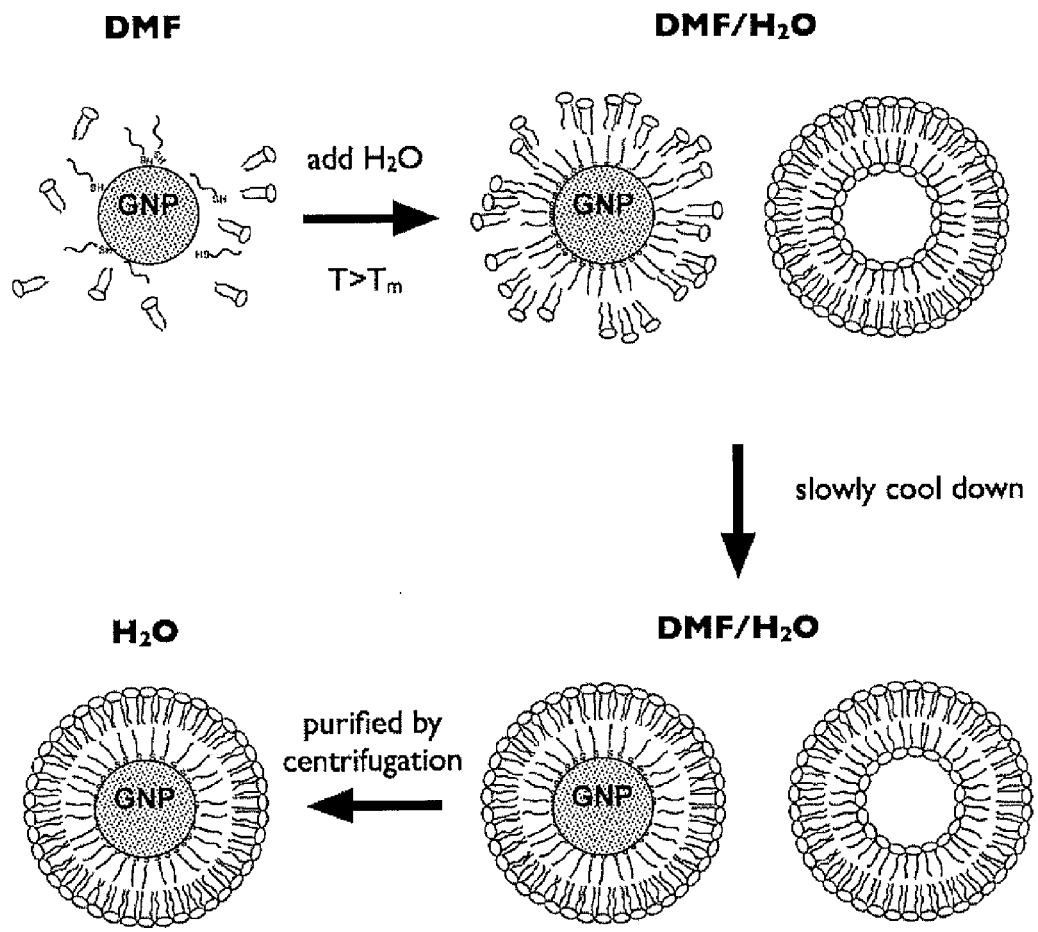
FIG. 2 schematically illustrates the preparation method of SERS signaling molecule.

The aforementioned preparation method is also illustrated in FIG. 2, in which the second intermediate composed of GNP, the thiol molecules and phospholipid and resolved in DMF (the left top drawing in FIG. 2) is adjusted to the appropriate volume ratio with ddH$_2$O, and the second intermediate is reacted at 80° C. for 1.5 hours (the right top drawing in FIG. 2). PLGNPs and hollow liposomes, etc. are formed after the gradually cooling down (the right down drawing in FIG. 2), and PLGNPs resolved in ddH$_2$O is obtained post centrifugation and purification (the left down drawing in FIG. 2). Although the GNPs act as the core in this preferred embodiment, the metal nanoparticles which are the same group with gold (such as silver nanoparticle, aluminum nanoparticle, platinum nanoparticle, etc.) or have the similar physiochemical properties also can be the material capped with phospholipid. The thiol molecule includes but not limit in 2-NAT, and other chemicals binding to the thiol group or has physiochemical property similar to 2-NAT also can act as the thiol molecule. Phospholipid includes but not limit in DPPC and DPPG, other molecules having similar structure or physiochemical property with DPPC or DPPG also can be the material for phospholipid, such as 1,2-dihexadecanoyl-sn-glycero-3-phosphoethanol-amine-N-[4-(p-maleimidomethy)cyclohexanecar-boxamide] (PE-MCC) or 1,2-di-oleoyl-sn-glycero-3-phosphocholine (DOPC).

II. Examination of PLGNP

Figure 3:
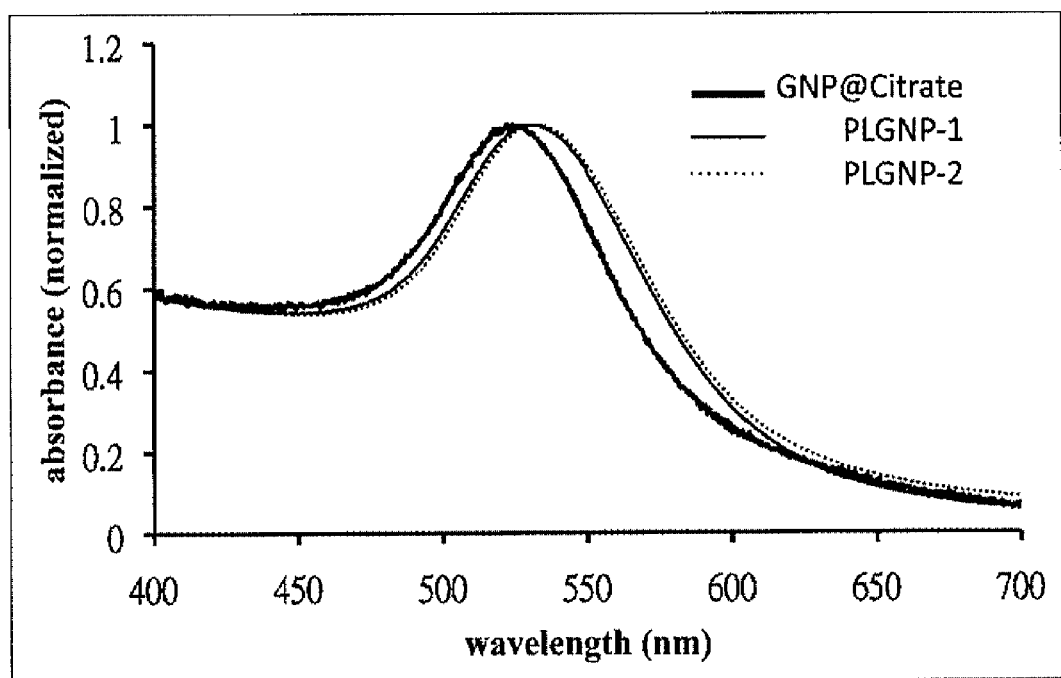
FIG. 3 represents the UV-VIS absorbance of GNP and PLGNPs (PLGNP-1 and PLGNP-2) under different wavelengths determined using UV-VIS spectrometer.

Next, the UV-VIS absorbance of GNP and PLGNPs (PLGNP-1 and PLGNP-2) under different wavelengths are determined using ultraviolet-visible light (UV-VIS) spectrometer, and the result is shown in FIG. 3. In FIG. 3, GNP shows the surface plasmon resonance absorbance characteristic at about 520 nm, but PLGNP-1 and PLGNP-2 presents that characteristic at 525 to 550 nm. Further, PLGNP-1 and PLGNP-2 prepared at different batches have the identical characteristics within the wavelength scope of FIG. 3. Therefore, PLGNP has significantly different surface plasmon absorbance characteristic from GNP due to the different structures between PLGNP and GNP.

Figure 4:
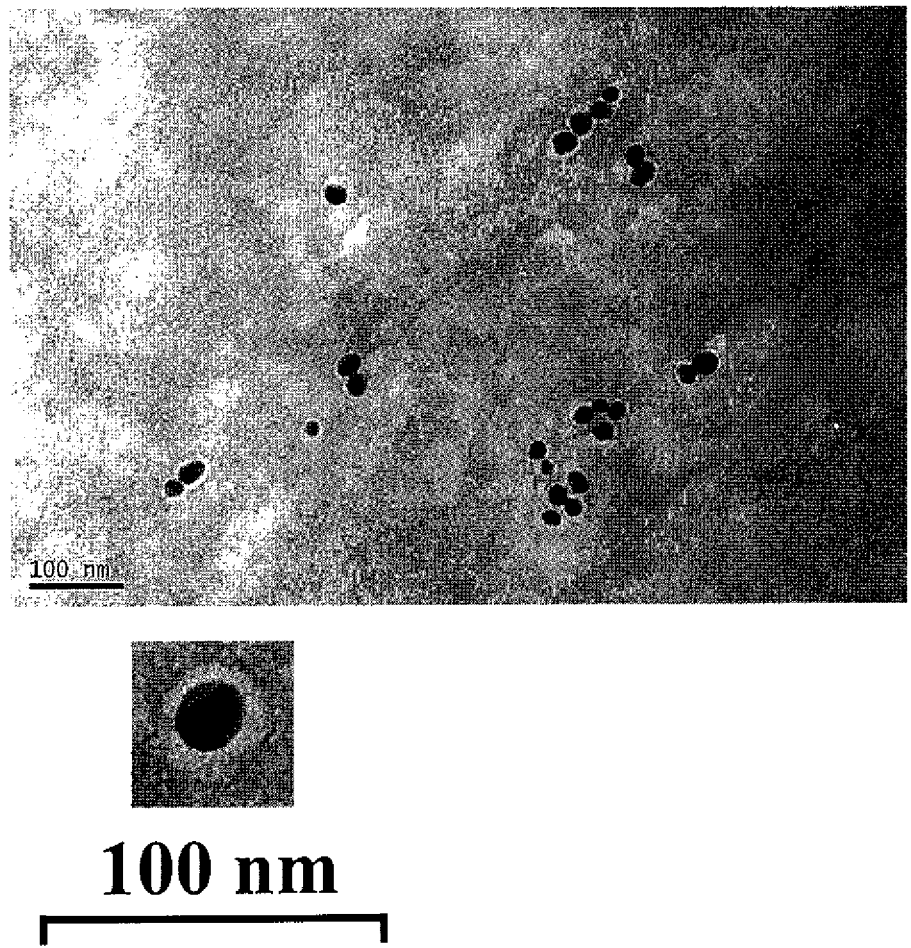
FIG. 4 represents a transmission electronic microscopic image of PLGNP with the negative staining treatment.

Please refer to FIG. 4, which shows an electronic microscopic image of PLGNP with the negative staining treatment. It can be known that each PLGNP actually is made by phospholipid-capped gold nanoparticle, the particle size of PLGNP still maintains at nano-size, and PLGNP does not generates the aggregated phenomenon made by the multiple GNPs.

Figure 5:
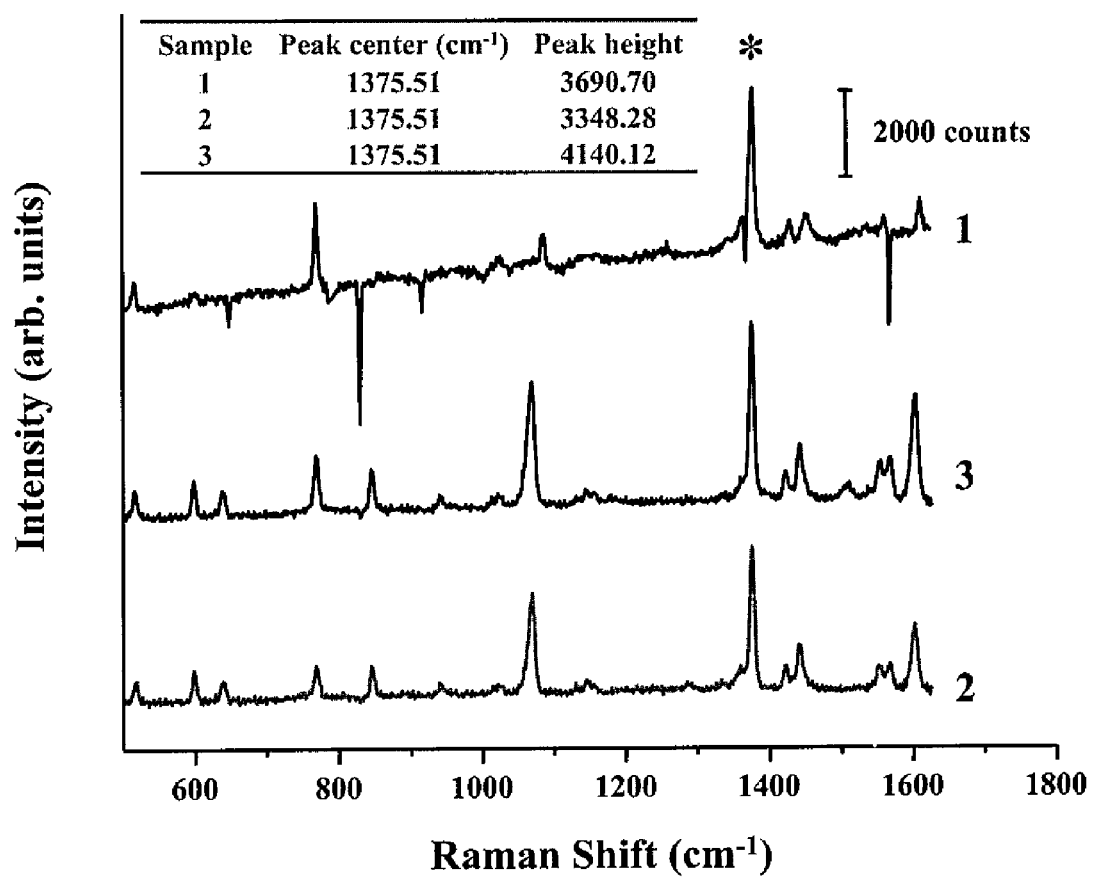
FIG. 5 represents the UV-VIS spectrum of the single dispersed PLGNP, wherein 25× concentrated 2-NAT is added to the slightly aggregated PLGNP upon preparation.

Please refer to FIG. 5, which shows the UV-VIS spectrum of the single dispersed PLGNP. The single dispersed PLGNP shows the Raman shift (i.e. the frequency difference between the scattering photon and the incident photon, also named as wave-number difference) at a frequency of 1375 cm$^{-1}$, and the corresponding molecular vibration energy is ranged between 3348.28 and 4140.12. Since the Raman scattering intensity after incident photons bombards to PLGNP accounts for $\frac{1}{1000}$ of Rayleigh scattering intensity and the Raman scattering directly determines the vibration spectroscopy of the molecular structure, PLGNP of the present invention still can determine Raman scattering and the molecular vibration energy. PLGNP of the present invention is able to be the effectively quantitative and qualitative detection tools. In particular, a trace amount of the test molecule in a sample can be determined using PLGNP technique.

The enhanced Raman scattering signaling molecule prepared in the present invention is made by a single GNP bound to the thiol molecule being encapsulated with phospholipid capping. Since the thiol molecule shows the characteristic of Raman scattering, PLGNP becomes a material having surface enhanced Raman scattering and can be applied on the detection device integrating optics and chemistry. PLGNP is relatively stable in the bio-system and is used in the detection of solutions containing salts or proteins, sera and cellular media and so on. PLGNP of the present invention can be widely applied on the fields of biomedicine, medical diagnosis and environment, etc.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for preparing a signaling molecule comprising a metal nanoparticle, the method comprising steps of:
    (a) treating a surface of the metal nanoparticle with an acidic solution;
    (b) resolving the metal nanoparticle in a dimethylformamide (DMF) to obtain a first intermediate;
    (c) adding a phospholipid to the first intermediate;
    (d) adding a thiol molecule to the first intermediate to perform a heating process to obtain a second intermediate; and
    (e) separating the second intermediate to obtain the signaling molecule comprising the metal nanoparticle.

2. The method according to claim 1, wherein the step (a) further comprising steps of:
    (a1) centrifuging the metal nanoparticle; and
    (a2) removing the acidic solution.

3. The method according to claim 2, wherein the step (a2) is performed by a decantation.

4. The method according to claim 1, wherein the step (d) further comprises a step of (d1) adding a water having a temperature the same in the step (c) to result in a water-DMF volume ratio of 1:1.

5. The method according to claim 1, wherein a preheating step is performed before the step (c).

6. The method according to claim 1, wherein the heating process in the step (d) is ranged between 60° C. and 100° C.

7. The method according to claim 6, wherein the heating process in the step (d) is performed at 80° C.

8. The method according to claim 1, wherein the step (e) is performed to remove a non-signaling molecule in the second intermediate by a centrifugation or a decantation.

9. The method according to claim 1, wherein the acidic solution is a citric acid solution.

10. The method according to claim 1, wherein the metal nanoparticle is one selected from a group comprising a gold, a silver, a aluminum and a platinum.

11. The method according to claim 10, wherein the metal nanoparticle is a gold nanoparticle.

12. The signaling molecule according to claim 1, wherein the phospholipid is selected from a group consisting of a dipalmitoylphosphophatidylcholine (DPPC), a dipalmitoylphos-phatidylglycerol (DPPG), a 1,2-dihexadecanoyl-sn-glycero-3-phosphoethanol-amine-N-[4-(p-maleimidomethy)cyclohexanecarboxamide] (PE-MCC), a 1,2-di-oleoyl-sn-glycero-3-phosphocholine (DOPC).

13. The method according to claim 12, wherein the phospholipid is DPPC-DPPG, which molar ratio is 14:1.

14. The method according to claim 12, wherein the phospholipid is resolved in the DMF.

15. The method according to claim 1, wherein the thiol molecule is a 2-naphthalenethiol.

16. The method according to claim 1, wherein the thiol molecule encapsulates a gold nanoparticle.

17. A signaling molecule prepared by the method of claim 1, comprising:
    a metal nanoparticle;
    a thiol molecule bound to a surface of the metal nanoparticle to form an inner layer; and
    a phospholipid capping the metal nanoparticle and the thiol molecule to form an outer layer,
    wherein a number of the metal nanoparticle is single, and the signaling molecule has a surface enhanced Raman scattering ability.

18. The signaling molecule according to claim 17, wherein the metal nanoparticle is one selected from a group comprises a gold, a silver, a aluminum and a platinum.

19. The signaling molecule according to claim 17, wherein the metal nanoparticle is a gold nanoparticle, and the thiol molecule is a 2-naphthalenethiol.

20. The signaling molecule according to claim 17, wherein the phospholipid is selected from a group consisting of a dipalmitoylphosphophatidylcholine (DPPC), a dipalmitoylphos-phatidylglycerol (DPPG), a 1,2-dihexadecanoyl-sn-glycero-3-phosphoethanol-amine-N-[4-(p-maleimidomethyl)cyclohexanecarboxamide] (PE-MCC), a 1,2-di-oleoyl-sn-glycero-3-phosphocholine (DOPC).

* * * * *